US010013530B2

(12) United States Patent
Marshall, DVM et al.

(10) Patent No.: US 10,013,530 B2
(45) Date of Patent: Jul. 3, 2018

(54) PET INSURANCE SYSTEM AND METHOD

(71) Applicant: Trupanion, Inc., Seattle, WA (US)

(72) Inventors: Kerri Marshall, DVM, Seattle, WA (US); Darryl Rawlings, Seattle, WA (US); Kathryn Plowman, Seattle, WA (US); Chris Cappelletti, Carnation, WA (US)

(73) Assignee: Trupanion, Inc., Seattle, WA (US)

( * ) Notice: Subject to any disclaimer, the term of this patent is extended or adjusted under 35 U.S.C. 154(b) by 0 days.

(21) Appl. No.: 14/924,606

(22) Filed: Oct. 27, 2015

(65) Prior Publication Data

US 2017/0039329 A1    Feb. 9, 2017

Related U.S. Application Data

(63) Continuation-in-part of application No. 14/210,079, filed on Mar. 13, 2014.

(60) Provisional application No. 61/801,404, filed on Mar. 15, 2013.

(51) Int. Cl.
G06Q 40/00     (2012.01)
G06F 19/00     (2018.01)
G06Q 10/10     (2012.01)
G06Q 40/08     (2012.01)

(52) U.S. Cl.
CPC .......... *G06F 19/328* (2013.01); *G06Q 10/10* (2013.01); *G06Q 40/08* (2013.01)

(58) Field of Classification Search
CPC ........ G06Q 40/08; G06Q 50/24; G06Q 50/22; G06Q 30/0238; G06Q 20/20; G06F 19/322

USPC .......................................................... 705/4
See application file for complete search history.

(56) References Cited

U.S. PATENT DOCUMENTS

| 5,720,502 | A  | 2/1998  | Cain |
| 6,117,526 | A  | 9/2000  | Marks |
| 6,966,064 | B1 | 11/2005 | Schneidewend et al. |
| 7,155,405 | B2 | 12/2006 | Petrovich |
| 7,266,770 | B2 | 9/2007  | Onbe et al. |
| D572,717  | S  | 7/2008  | Loehr et al. |
| 7,496,583 | B2 | 2/2009  | Moore et al. |
| D605,653  | S  | 12/2009 | Danton |
| 8,341,547 | B2 | 12/2012 | Ingman et al. |
| 8,359,605 | B2 | 1/2013  | Ross |

(Continued)

FOREIGN PATENT DOCUMENTS

JP    2002-073802 A    3/2002
JP    2013-022984 A    2/2013
(Continued)

OTHER PUBLICATIONS

PCT International Search Report of PCT/US14/27042; dated Oct. 1, 2014 (4 pgs.).

(Continued)

*Primary Examiner* — Reginald R Reyes
(74) *Attorney, Agent, or Firm* — Wilson Sonsini Goodrich & Rosati

(57) ABSTRACT

This disclosure relates to a system and method implemented to facilitate real-time medical coverage for veterinary hospitals. More specifically, the disclosure as a pet medical insurance system and method utilizes data available in veterinary hospital practice information systems to facilitate real-time insurance enrollment and claims processing.

22 Claims, 20 Drawing Sheets

(56) References Cited

U.S. PATENT DOCUMENTS

| | | |
|---|---|---|
| D777,737 S | 1/2017 | Marshall et al. |
| 2003/0004740 A1 | 1/2003 | Dickey et al. |
| 2004/0254816 A1 | 12/2004 | Myers |
| 2005/0060344 A1 | 3/2005 | Pawlick |
| 2005/0091606 A1 | 4/2005 | Sauermann |
| 2006/0074724 A1* | 4/2006 | Schwartz ............... G06Q 40/08 705/4 |
| 2006/0075724 A1 | 4/2006 | Kammler et al. |
| 2006/0196436 A1 | 9/2006 | Nichols |
| 2006/0251775 A1 | 11/2006 | Anderson et al. |
| 2007/0084099 A1 | 4/2007 | Sarbo et al. |
| 2007/0203758 A1* | 8/2007 | Stephens ............... G06Q 10/10 705/4 |
| 2008/0172617 A1 | 7/2008 | Takeda et al. |
| 2008/0307339 A1 | 11/2008 | Boro et al. |
| 2009/0106678 A1 | 4/2009 | Chase et al. |
| 2009/0182586 A1* | 7/2009 | Cohane ............... G06Q 20/102 705/4 |
| 2009/0289844 A1 | 11/2009 | Palsgrove et al. |
| 2009/0300540 A1 | 12/2009 | Russell |
| 2010/0017234 A1 | 1/2010 | Stephens et al. |
| 2010/0293487 A1 | 11/2010 | Schoenberg |
| 2011/0131507 A1 | 6/2011 | Butcher |
| 2012/0060105 A1 | 3/2012 | Brown et al. |
| 2012/0110453 A1 | 5/2012 | Ma et al. |
| 2012/0265702 A1 | 10/2012 | Maher |
| 2013/0218592 A1 | 8/2013 | Hashmat |
| 2014/0155785 A1 | 6/2014 | Haas |
| 2014/0278551 A1 | 9/2014 | Marshall et al. |

FOREIGN PATENT DOCUMENTS

| | | |
|---|---|---|
| WO | WO-2006036316 A1 | 4/2006 |
| WO | WO-2014152179 A2 | 9/2014 |
| WO | WO-2017075207 A1 | 5/2017 |

OTHER PUBLICATIONS

PCT Written Opinion of the International Searching Authority of PCT/US14/27042; dated Oct. 1, 2014 (7 pgs.).

European search report dated Dec. 9, 2016 for EP Application No. 14770490.

International search report with written opinion dated Nov. 29, 2016 for PCT/US2016/059095.

U.S. Appl. No. 14/210,079 Final Office Action dated Sep. 5, 2017.

U.S. Appl. No. 14/210,079 Non-Final Office Action dated Dec. 7, 2016.

U.S. Appl. No. 14/210,079 Non-Final Office Action dated Mar. 21, 2018.

U.S. Appl. No. 29/449,619 Final Office Action dated Jul. 17, 2015.

U.S. Appl. No. 29/449,619 Non-Final Office Action dated Oct. 3, 2014.

U.S. Appl. No. 29/449,619 Notice of Allowance dated Sep. 13, 2016.

* cited by examiner

FIGURE 8B

PET INSURANCE SYSTEM AND METHOD

PRIORITY CLAIMS/RELATED APPLICATIONS

This application claims priority under 35 USC 120 and is a continuation in part of U.S. patent application Ser. No. 14/210,079, filed on Mar. 13, 2014 and entitled "Pet Insurance System and Method" which in turn claims priority to and the benefit under 35 USC 119(e) and 120 of U.S. Patent Application Ser. No. 61/801,404, filed on Mar. 15, 2013 and entitled "Pet Insurance System and Method", the entirety of which is incorporated herein by reference.

BACKGROUND

Veterinary hospitals provide many medical services during the course of caring for a patient. Pet insurance is one of these many services. Often, patients have health problems that require veterinary care above and beyond what a pet owner is prepared to pay out-of-pocket at the time services are provided, even when they have pet insurance coverage. The pet owner files a claim after leaving the veterinary practice and receives notice of coverage, eligibility and payment, if applicable, from the insurance company. These processes and systems are cumbersome and do not allow a pet owner to rapidly obtain or utilize pet medical insurance.

For the veterinary hospital, existing systems do not provide them with real-time, accurate information about the status of a pet's insurance policy, eligibility of coverage, status of a claim, or facilitate the offering of pet insurance coverage. Most systems are not responsive enough to effectively aid a veterinary practice in managing their practice, frustrating the hospital and the pet owner with the delay.

Additionally, due to the delay in claims processing and the need for the pet owner to cover the expense of medical services at time of service and prior to being reimbursed by the insurance company, the hospital must often provide alternate courses of care that are less expensive, more affordable for pet owners. This is counter-intuitive to the purpose of pet medical insurance coverage.

Thus, it is desirable to provide a pet medical insurance system and method to overcome the above limitations and it is to this end that the disclosure is directed. It is also within the scope of the disclosure to facilitate medical coverage and services at veterinary hospitals outside of pet insurance, such as wellness plans, radiology and lab, and similar services provided at veterinary hospitals utilizing the same system and method implementation.

BRIEF DESCRIPTION OF THE DRAWINGS

The disclosure will be better understood if reference is made to the accompanying drawings, in which:

FIGS. 8A and 8B illustrate an example of a user interface for tracking insurance offers;

DETAILED DESCRIPTION OF ONE OR MORE EMBODIMENTS

The disclosure is particularly applicable to a cloud computing architecture pet insurance system and it is in this context that the disclosure will be described. It will be appreciated, however, that the system and method has greater utility.

In the disclosure set forth below, a pet owner is a guardian of the pet and could be the pet owner, pet sitter, or similar pet guardian. In the disclosure set forth below, a patient refers to an animal being treated by a veterinary practice. A patient also may be referred to as "pet". In the disclosure below, a veterinary practice refers to a hospital, clinic or similar where services are provided for an animal.

Figure 1:
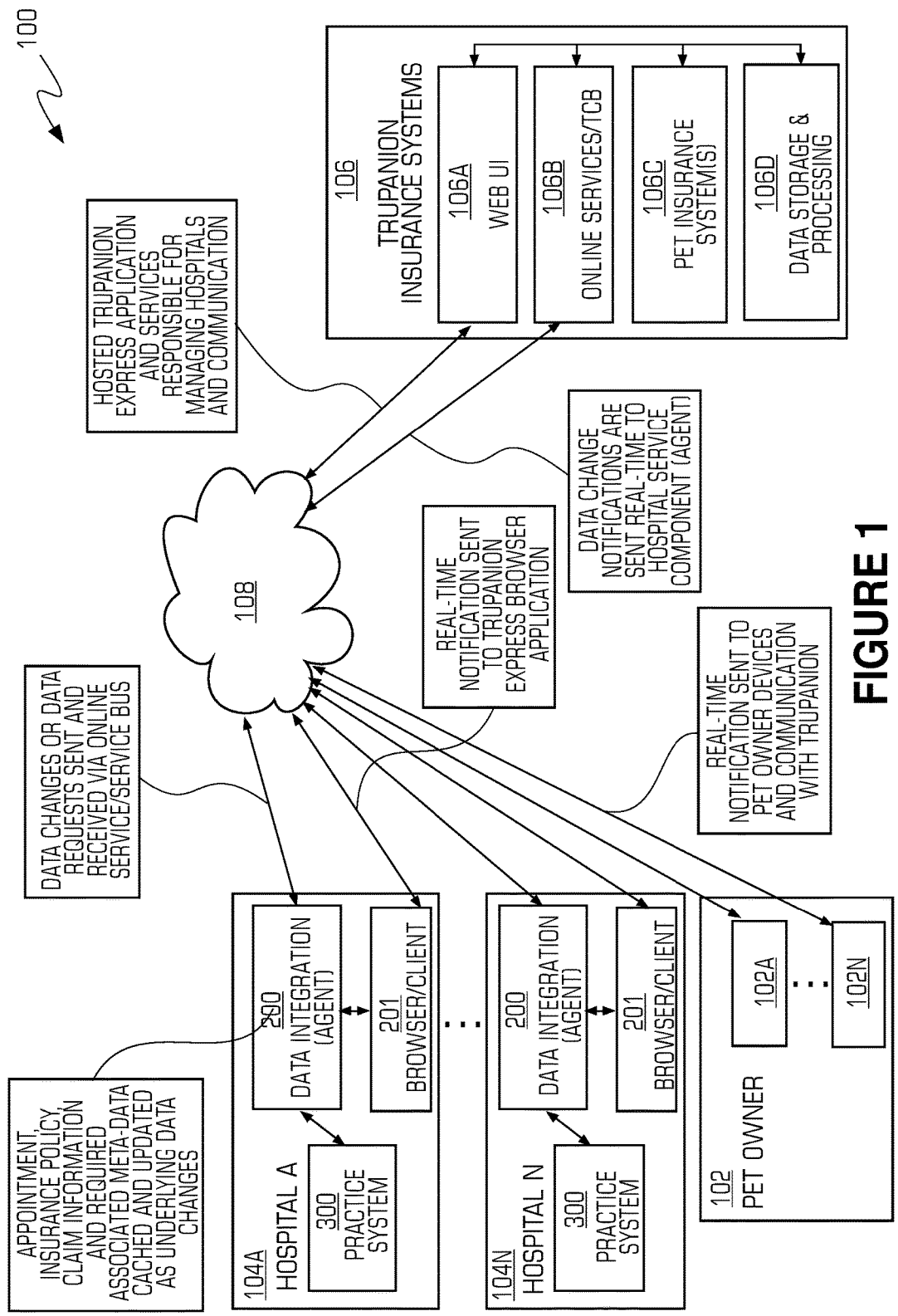
FIG. 1 is a diagram of an implementation of a pet medical insurance system.

FIG. 1 is a diagram of an implementation of pet insurance system (100). The implementation in FIG. 1 is cloud computing architecture. However, the system may be implemented in a client/server architecture, a mainframe architecture, a software as a service model and the like, all of which are within the scope of this disclosure. The system may include one or more computing devices (102) and each computing device may be used by a pet owner to connect to and interact with the pet insurance backend component (106) over a communication path (108). The system may also have one or more computing devices (104), such as 104A, . . . , 104N and each computing device may be used by (or integrated into) a veterinary practice and allow the veterinary practice to interact with a pet insurance backend component (106) or the communications path (108). Each computing device (102, 104) may be a processor based device with storage, memory, a display and wireless or wired connectivity circuits that allow the computing device (102, 104) to interact with the backend component (106). For example, each computing device may be a smartphone device, such as a device operating using the iOS, Android or Symbian operating systems, a personal computer, a client/server system, a terminal, a tablet computer, a cellular phone and any other device that would be capable of interacting with the backend component (106). In one implementation, each of the computing device 104 may have a data integration agent (200) and a client (201) that interacts with the backend component (106). In one implementation, the data integration agent (200) and the client (201) may be a plurality of lines of code executed by the processor of the computing device. In one implementation, each of the computing device 102, 104 may have a browser that interacts with the backend component (106), displays web pages and allows the user to enter information into forms. In one implementation, the browser may be a plurality of lines of computer code executed by the processor of the computing device 102, 104.

The communication path (108) may be a wired or wireless network that may be unsecure or secure and uses typical protocols for the exchange of data between the computing devices 102, 104 and the backend component (106). For example, the communication path 108 may be an Ethernet network, the Internet, a wireless cellular network, a wireless digital data network and the like or any combination thereof and the system is not limited to any particular communication path 108. In the implementation in which the communication path 108 is the Internet, the communication path 108 may use the known HTTP or HTTPS protocol for data communications.

The backend component 106 may be implemented as one or more computing resources or hardware devices. In one implementation, the backend component 106 may be one or more server computers, one or more cloud computing resources and the like and each resource has one or more processors, memory, persistent storage and the like. The backend component 106 may further comprise a web server (106A), online services (106B), a pet insurance management component (106C), and data storage and processing (106D) that are coupled together as shown in FIG. 1. The web server (106A), that may be implemented as a hardware web server or a software implemented web server, may generate and exchange web pages with each computing device 102, 104 that is using a browser. The online services—Trupanion Central Services, or TCS—(106B), may be implemented as a plurality of lines of computer code and may generate or exchange information with computing devices 102, 104 directly or through communication path 108 utilizing SignalR, ServiceBus, or similar notification services. The pet insurance management component (106B) may be implemented as a plurality of lines of computer code that are stored in the computing resources and then executed by the processor(s) of the computing resources to implement the pet insurance management functions that are described below in more detail. The data processing and storage device (106D) may be a hardware storage device or a software implemented storage device, such as a database, that stores user and veterinary practice information for the system, stores information about each insurance offer, stores information about each pet that is enrolled in the pet insurance system, and stores the information about each pet insurance claim in the system.

Figure 2:
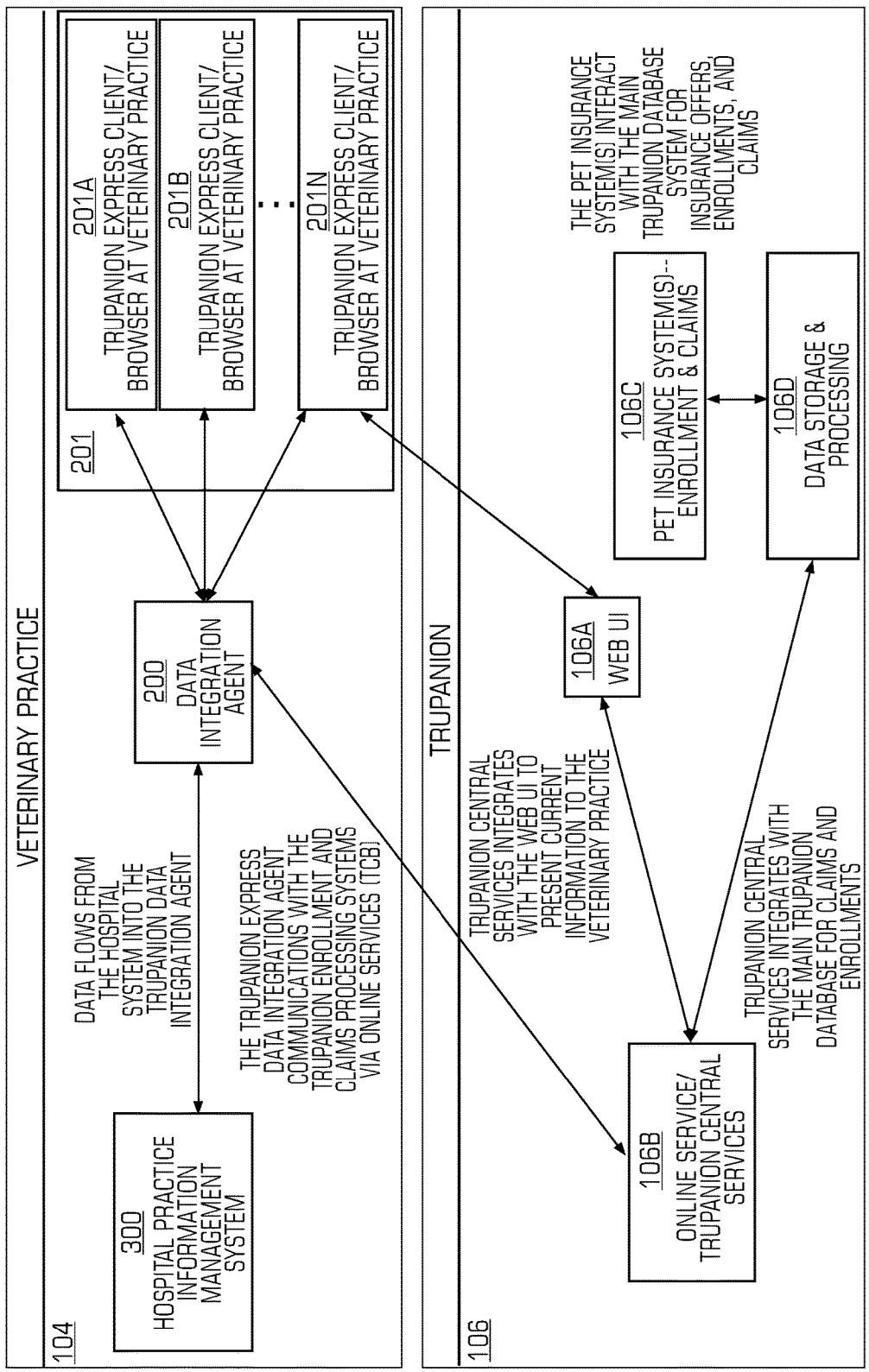
FIG. 2 illustrates more details of the pet medical insurance system.

FIG. 2 illustrates more details of the pet insurance system and in particular the components in each veterinary practice computing device 104 and the backend component 106 and the interactions between the two. As shown the veterinary practice may have one or more browsers/clients (201), a hospital practice information management system (300), and a data integration agent (200). As shown, data from the hospital practice information management system (300) flows into the data integration agent (200) and the data integration agent (200) connects to and communicates with the backend component (106). The data integration agent (200) also connects to and communicates with one or more client/browsers (201) in the computing devices 104. In one implementation, each of the components of the veterinary practice computing device 104 may be a plurality of lines of computer code that are executed by a processor of the computing device 104. The Hospital Practice Information Management System (PIMS) is an existing system used by a veterinary practice that use database and visualization technologies (user interface) with the aim to support various hospital/patient management and administration tasks. Different PIMS manufacturers include different modules that allow for many common hospital technology requirements that may include inventory tracking, procedure codes, connection to diagnostic equipment and service providers, connection to a variety of radiology modalities and services, and invoice generation.

The data integration agent (200) may be provided by the pet insurance backend system (106) and may be installed in the computing device 104 of the veterinary practice. The data integration agent (200) is a system which integrates with these varied systems to provide added value and operational simplicity for employees of the veterinary practice and pet owners. The data integration agent is responsible for retrieving and mapping data from the PIMS (300), sending communications to and receiving information from Trupanion Central Services (106B) about claim, insurance offers, and enrollments, and communication with the Trupanion Express clients/browsers (201). The data integration agent (200) employs various technological mechanisms to limit traffic between Trupanion Central Services (106B) and Trupanion Express clients/browsers (201), as well as the PIMS (300), creating efficient correspondence between all systems. The data integration agent (200) may include an abstracted engine that allows communication with various PIMS systems on the market today, as well as the ability to integrate with additional in the future in a plug-and-play fashion.

The client/browser 200, is the user interface for Trupanion Express. It communicates with the data integration agent (200) and the web UI (106A) with the aim to exchange information between the hospital and the backend component (106). The client/browser allows submitting claims, issuing insurance offers, searching PIMS data for clients, appointments, mapping clients between systems, and displaying all of the information for these activities in a digestible way for veterinary practice employees—resulting in improved patient care.

The backend component (106) may further comprise a services component (106B), that may be known as Trupanion Central Services, a data storage and processing component (106D), and a pet insurance system(s) (106C), that may be comprised of enrollment and claims systems that are coupled together as shown in FIG. 2. Sample data is included in the below table:

| Sample Data Exchanged Between the Veterinary Practice & Trupanion | Enrollment Sample Data | Claims Sample Data |
| --- | --- | --- |
| Patient demographics<br>Client demographics<br>Claim form information<br>Invoices/estimates<br>Medical record information<br>Insurance offer information | Policy ID & type<br>Policy status<br>Enrollment veterinary practice information<br>Policy coverage details | Claims basics<br>Claiming veterinary practice information<br>Claim outcomes & amount covered<br>Claims payments |

In one implementation, each of the components of the backend (106) may be a plurality of lines of computer code that are executed by a processor of the computing device 106. The services component (106B) integrates with data storage and processing (106D). The enrollment processing system and claims processing system—pet insurance systems 106C—may interact with the data storage and processing systems (106D) allowing insurance offers to be issued and activated and claims to be processed. The services component (106B) is a service inside Trupanion's network and processes requests from and sends information to the data integration agent (200) and passes appropriately formed requests to the data storage & processing systems (106D). The data storage and processing system (106D) is any location where transactional data for Trupanion's various IT systems is processed and/or stored. The pet insurance system (106C) is comprised of the enrollment processing system, the system that issues insurance offers to pet owners, and the claims processing system, the system that catalogs the collection of medical records that enables claims adjudicators to manage and process pet owner claims. The pet insurance system (100) is revolutionary in that it enables claims to be adjudicated very quickly—allowing the pet owner to not pay out-of-pocket expenses at the veterinary practice. Said another way, the pet insurance system (100) allows Trupanion to pay the veterinary hospital directly with the invoice while the customer is waiting to checkout, similar to the concept of "co-pay" in human health care. The pet insurance system (100) allows for near real-time claims submission and claims processing, enabling claim adjudication at point-of-sale at the veterinary practice. A typical system uses typical channels such as fax or mail that support a delayed reimbursement model for veterinary practices and/or pet owners.

Figure 3:
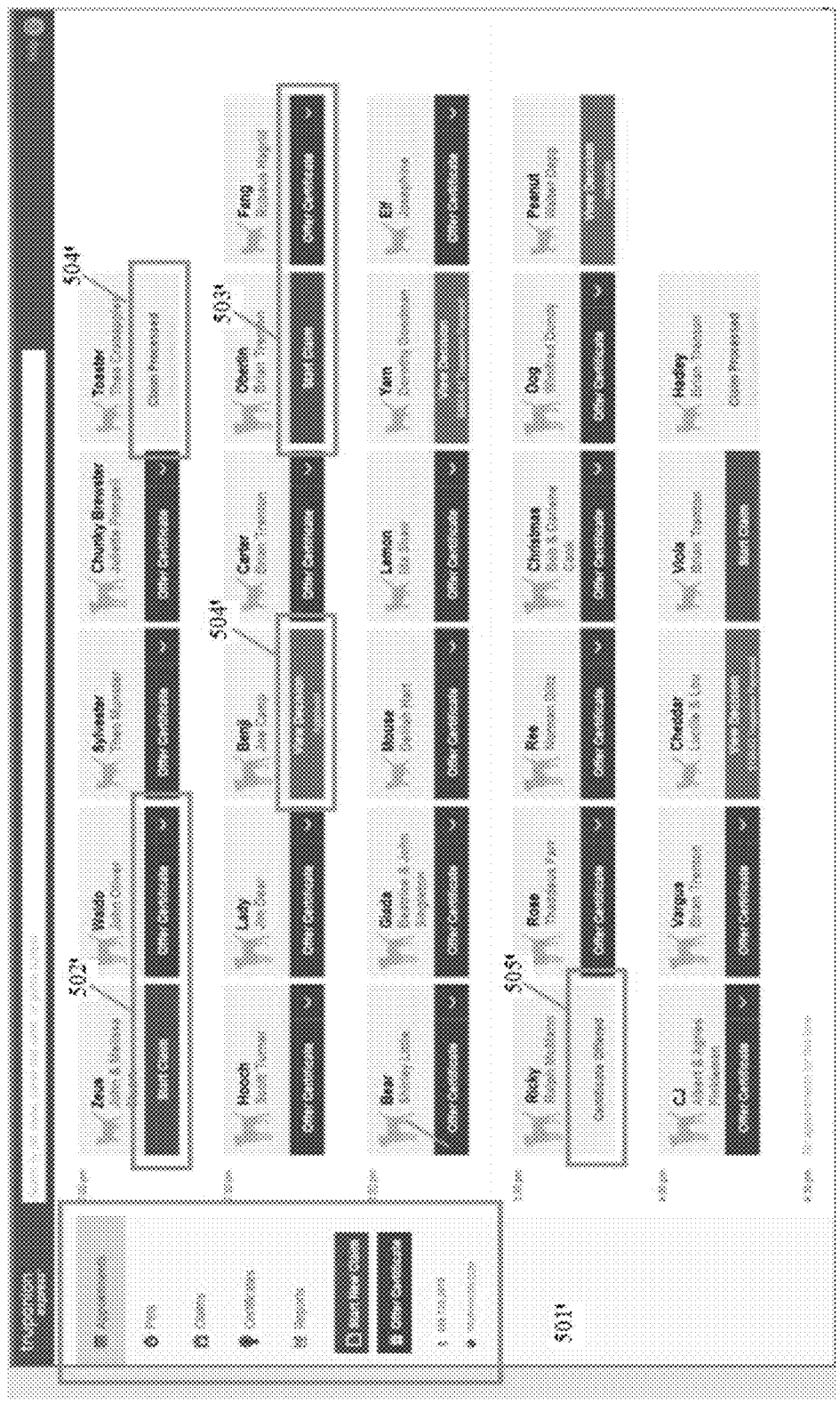
FIG. 3 illustrates an example of a user interface of the pet medical insurance system.

FIG. 3 illustrates an example of a user interface 500 of the pet insurance system. The user interface may include a navigation portion (501) that allows the user to navigate around to various parts of the pet insurance system user interface. The user interface may include a status (502) for each pet to indicate the current coverage of that pet. The user interface may further include an action button (503) allowing the user to submit claims or issue an insurance offer to a selected pet. The user interface may have status indicators for current claims transactions (504). The user interface may also have status indicators for current offers of insurance (505).

Figure 4:
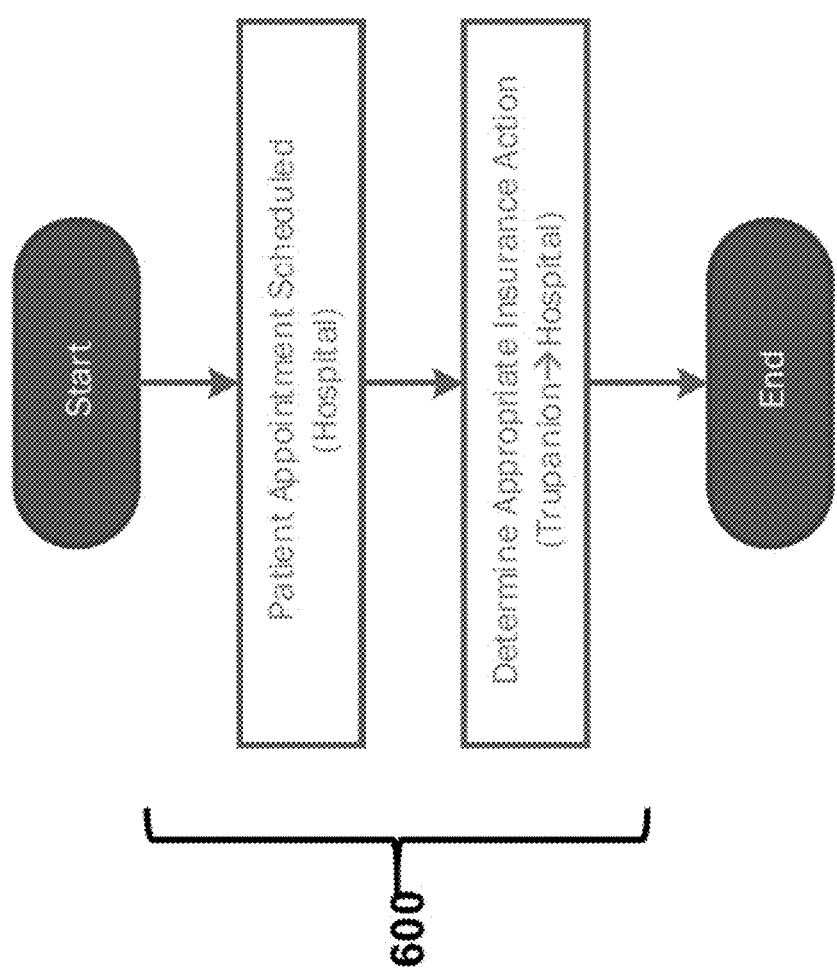
FIG. 4 illustrates a method of interacting with hospital appointment information and providing insurance action options.
Figure 5:
FIG. 5 illustrates an example of a user interface of appointment data and insurance interaction.

FIG. 4 illustrates a method (600) for determining the current pet insurance coverage for patient with scheduled appointments in the hospital practice information management system (300) and displaying the appropriate action in the pet insurance system user interface (500). FIG. 5 illustrates an example of a user interface displaying the appropriate insurance based on the method illustrated in FIG. 4.

Figure 6:
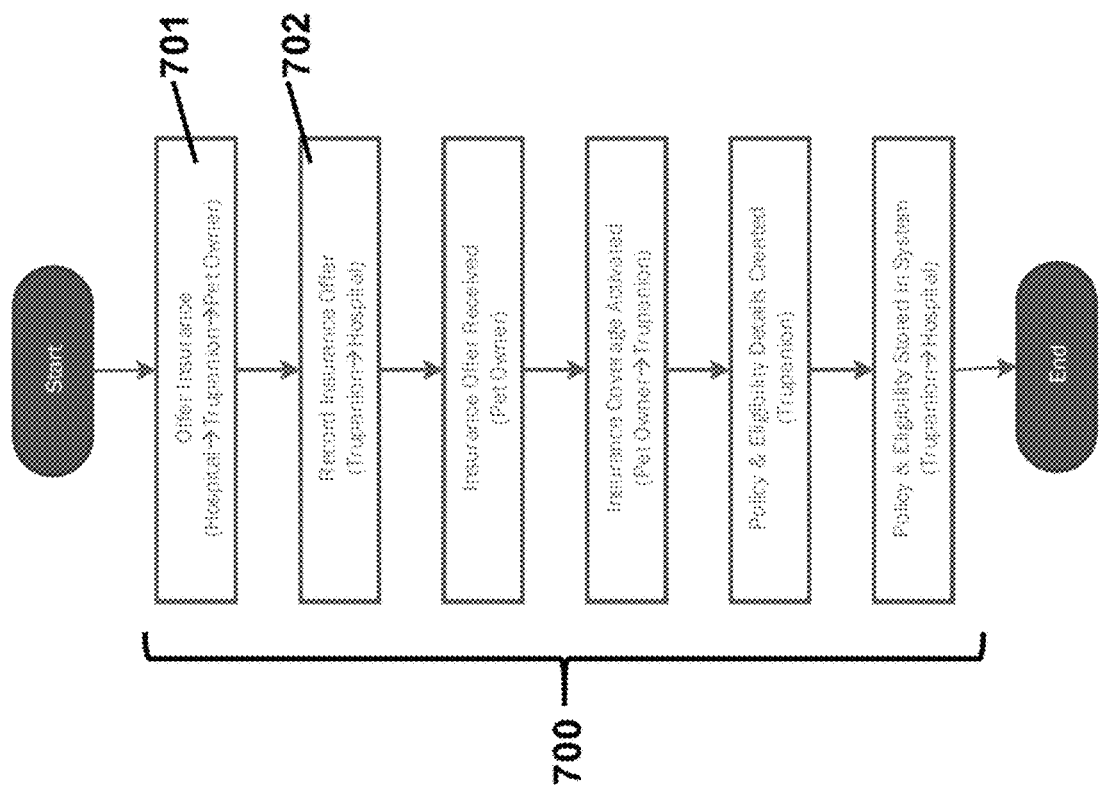
FIG. 6 illustrates a method for offering insurance, tracking insurance offers, and providing insurance coverage and eligibility details.
Figure 7:
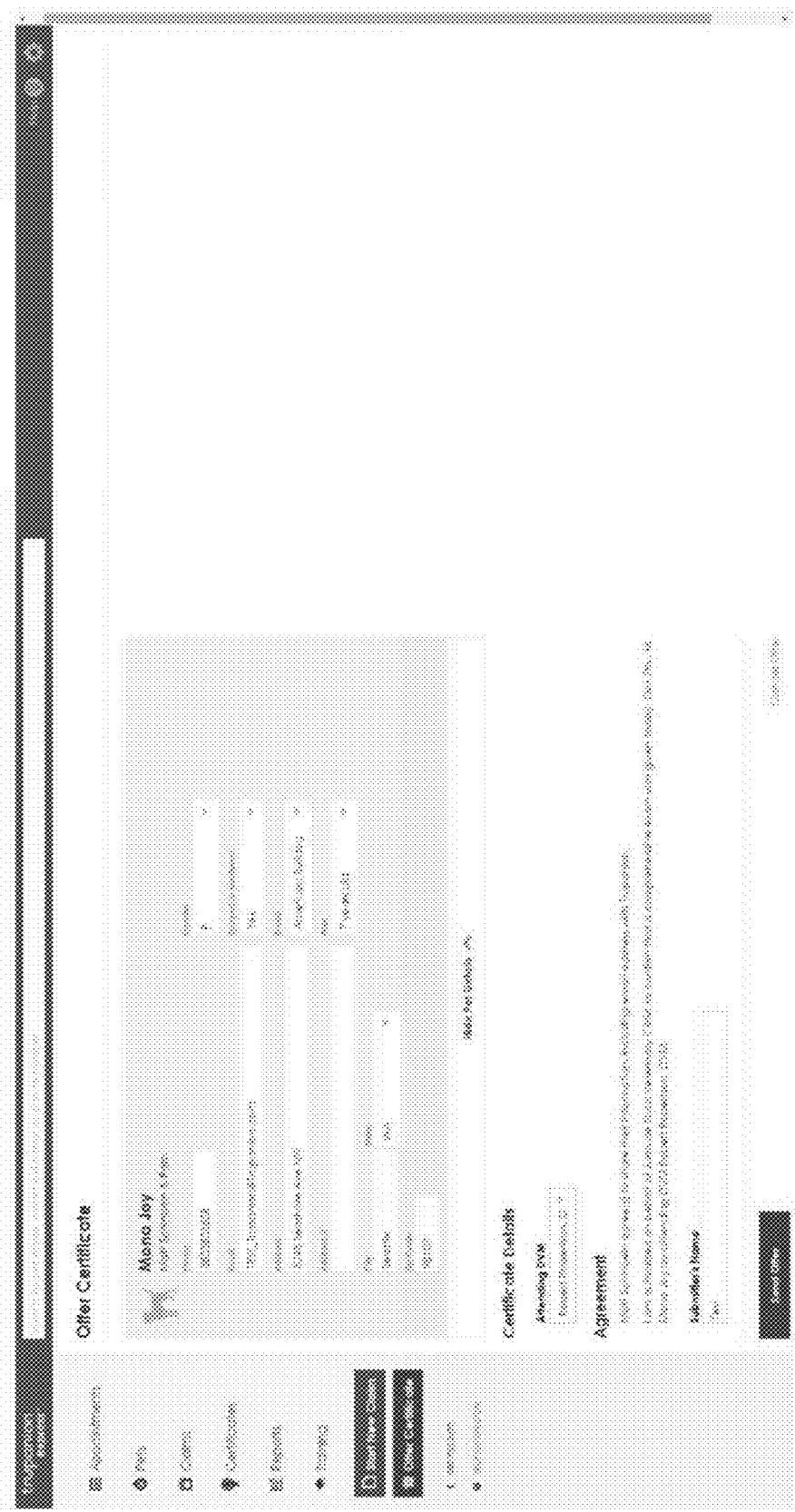
FIG. 7 illustrates an example of a user interface for offering pet insurance coverage to a pet owner.

FIG. 6 illustrates a method (700) for obtaining insurance and tracking insurance offers using the pet insurance system and FIG. 7 illustrates an example of a user interface for offering pet insurance to a pet owner. The pet insurance system makes it easier for a pet owner to get pet insurance and then quickly be able to have proof of the pet insurance in the form of an insurance offer that can be presented to the veterinary practice to establish the insurance of the pet. In the method (700), a veterinary practice may provide a pet owner an insurance offer (701) which is recorded in Trupanion systems (702) through the data integration agent (200). When the veterinary practice offers the insurance to the pet owner, an employee of the veterinary practice may enter the insurance offer into the client (201), such as shown in FIG. 7, and the information about the insurance offer is passed onto the backend component 106 through the data integration agent (200). The pet owner, using a computing device 102, may then activate the insurance offer, and obtain pet insurance, using an email link or by phone which is sent to the backend component 106. Once the pet owner activates the insurance coverage, the pet owner receives proof of insurance which is also passed back to the veterinary practice through the data integration component 200 so that the veterinary practice receives quick notice of the insurance for the pet. In addition, since the computing device 104 and the backend component 106 are integrated as shown in FIG. 2, all parties involved are rapidly notified of changes to the pet's insurance coverage. For example, this means the veterinary practice can be comfortable that the pet has insurance for the procedure that is about to be performed. The system may also display the treatment or procedure that is, has been or will be performed on a particular patient or by a particular employee at the veterinary practice.

Figure 8A:
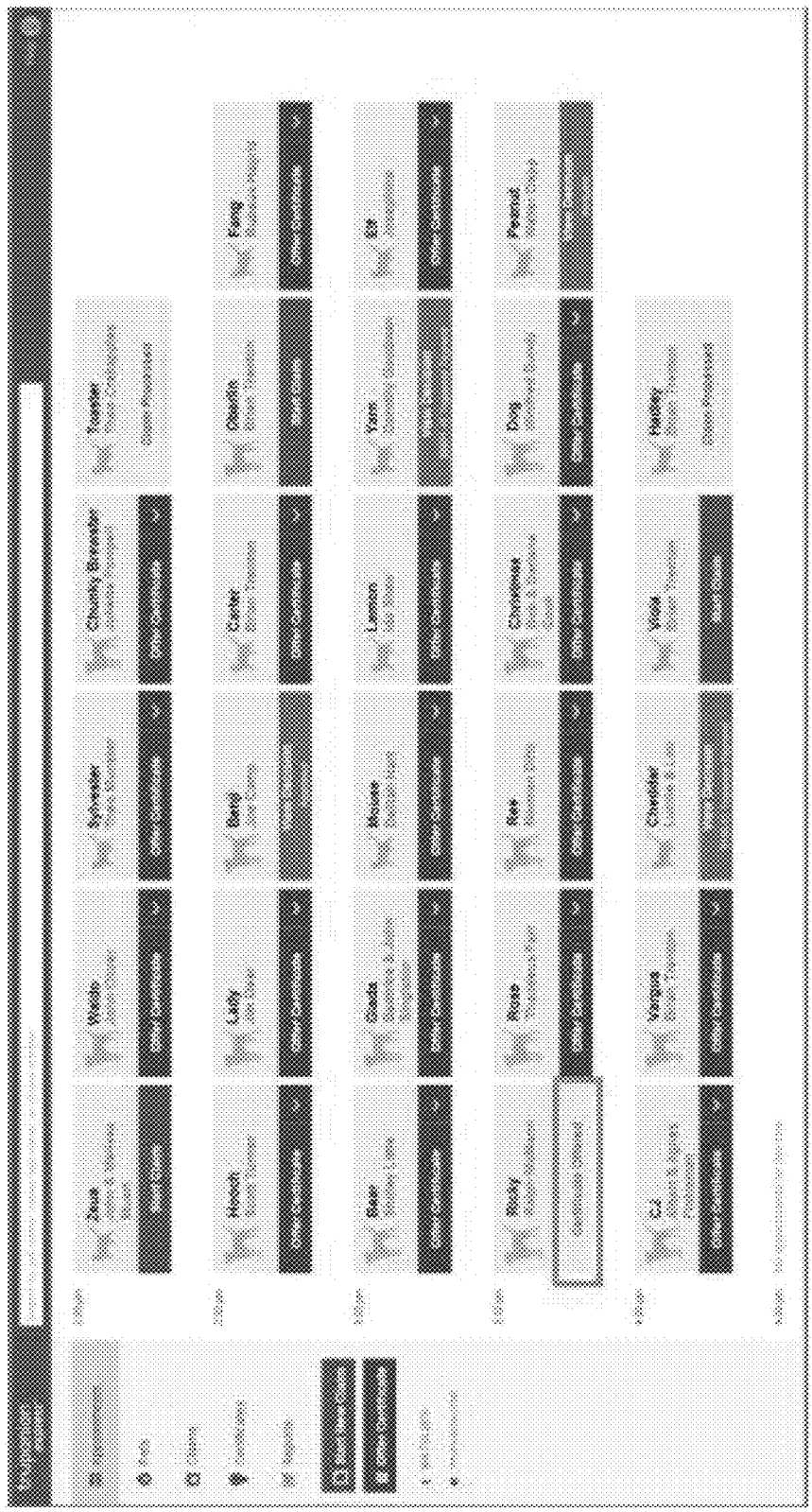
Figure 8B:
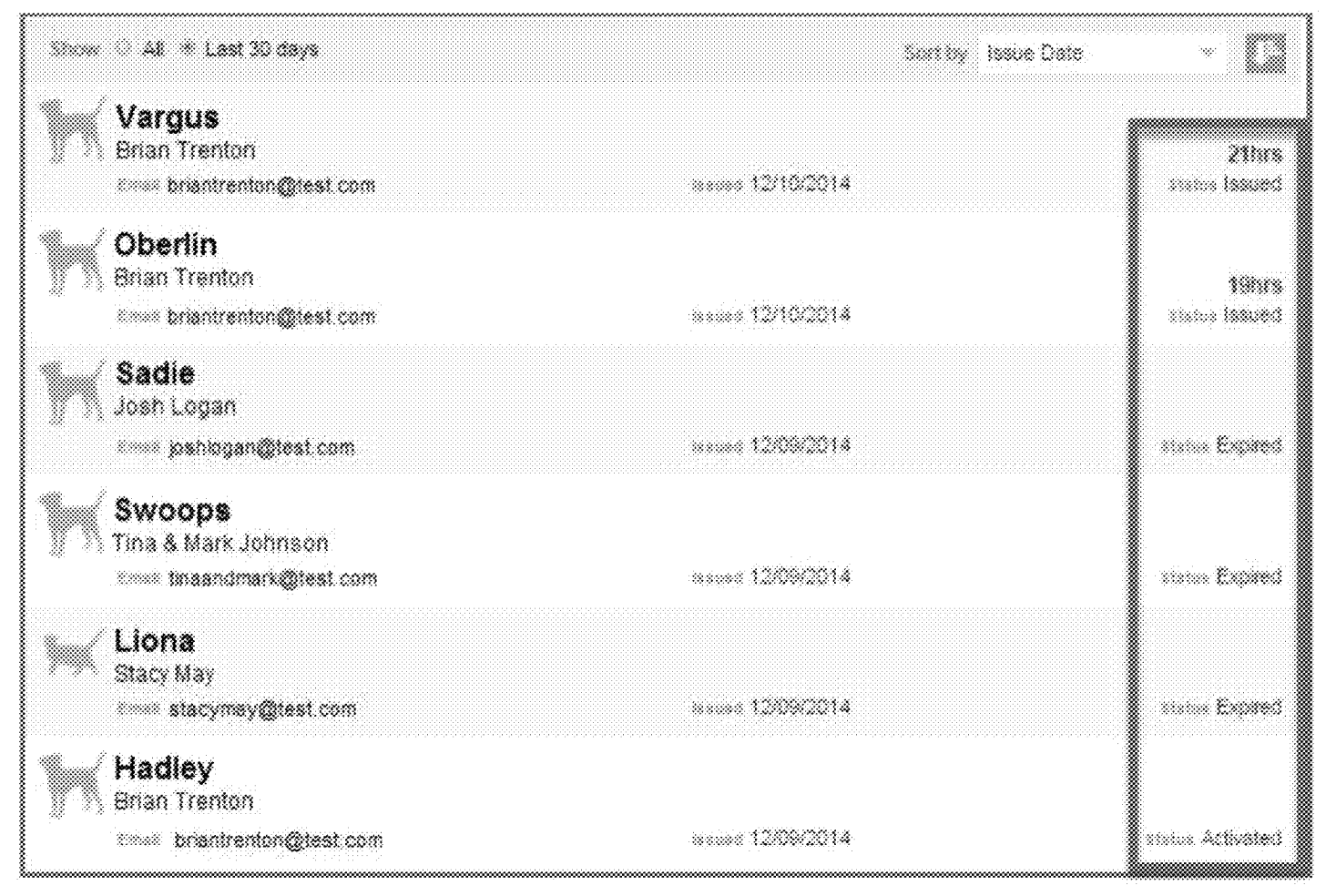
Figure 9:
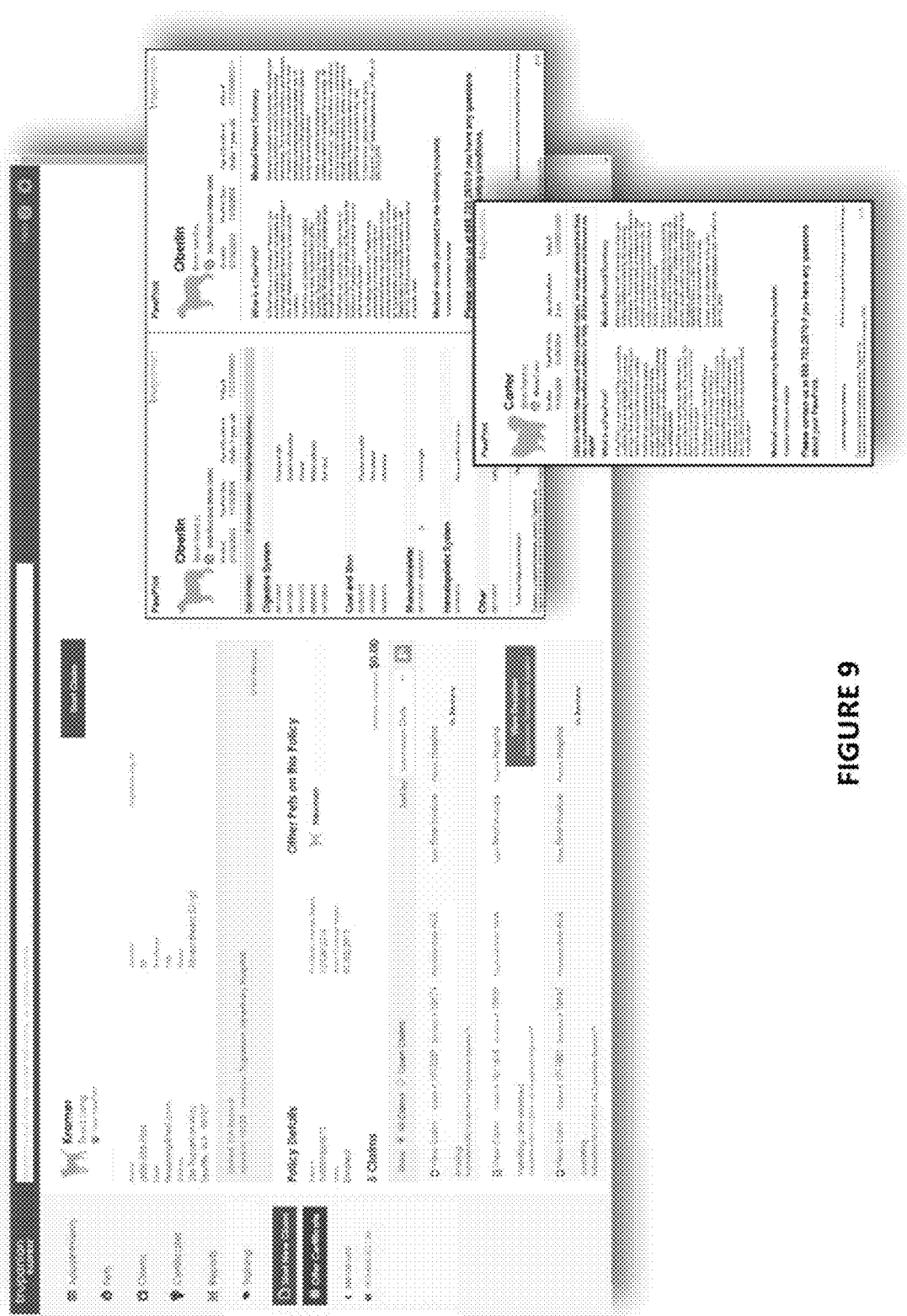
FIG. 9 illustrates an example of a user interface displaying the status of a particular pet's medical insurance coverage and eligibility.

FIGS. 8A and 8B illustrate examples of a user interface for tracking pet insurance offers through the pet insurance system user interface in the client/browser (201) in the veterinary practice. FIG. 9 illustrates an example of a user interface of a particular pet's insurance coverage eligibility once the insurance offer has been activated.

Figure 10:
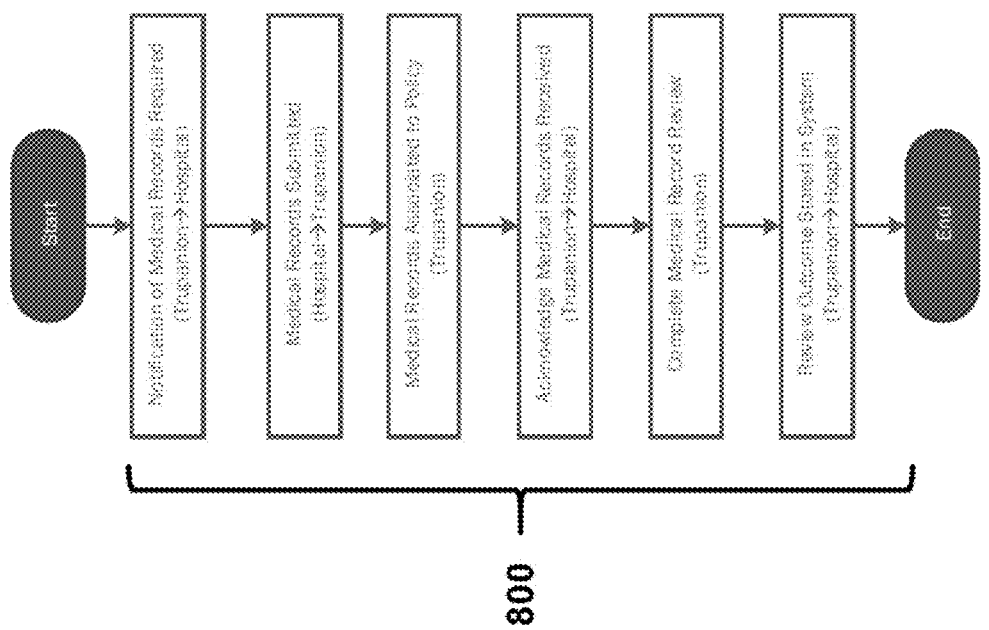
FIG. 10 illustrates a method for requesting and receiving medical record information.
Figure 11A:
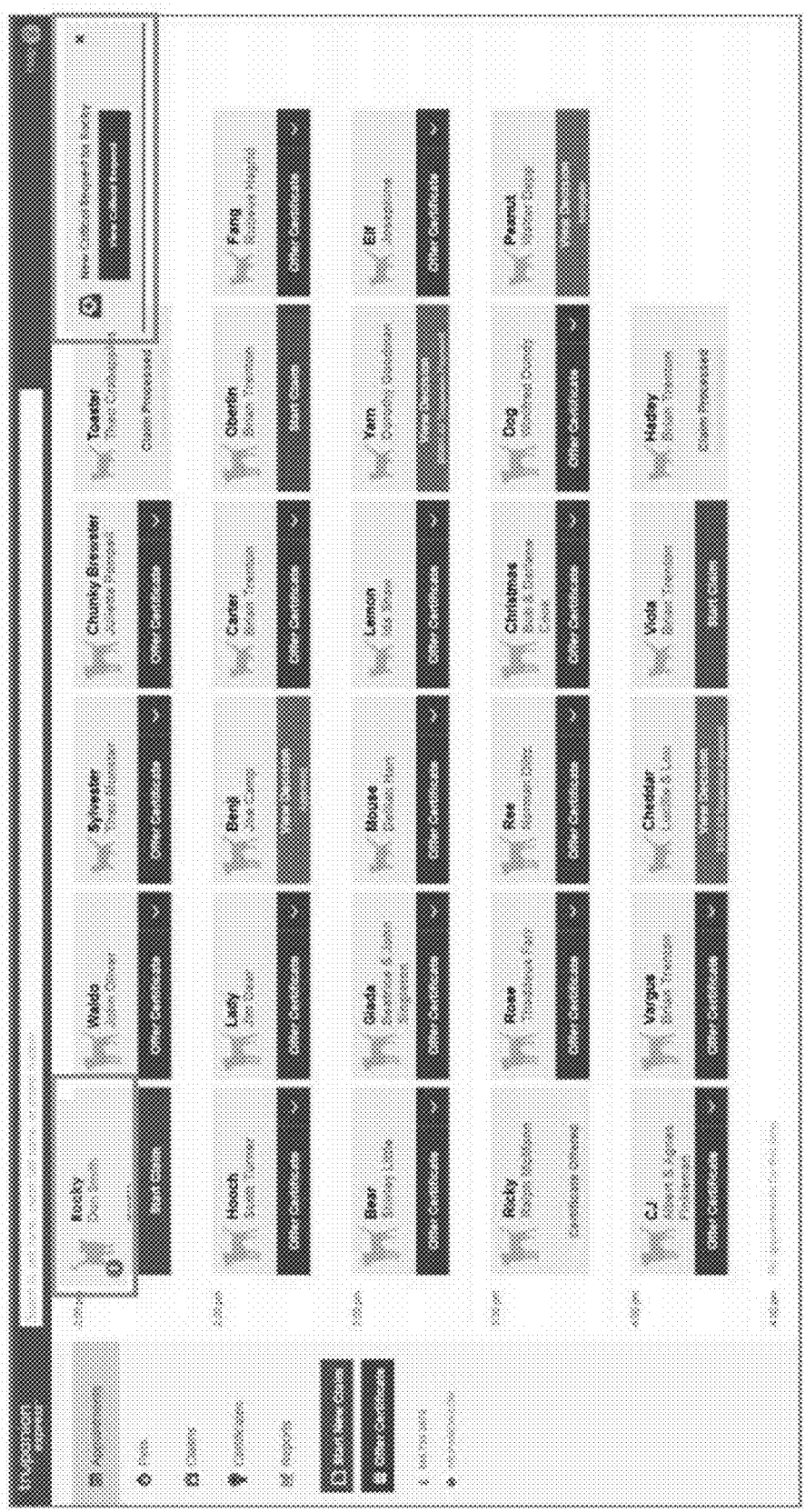
FIGS. 11A and 11B illustrates an example of a user interface for medical records requests.
Figure 11B:
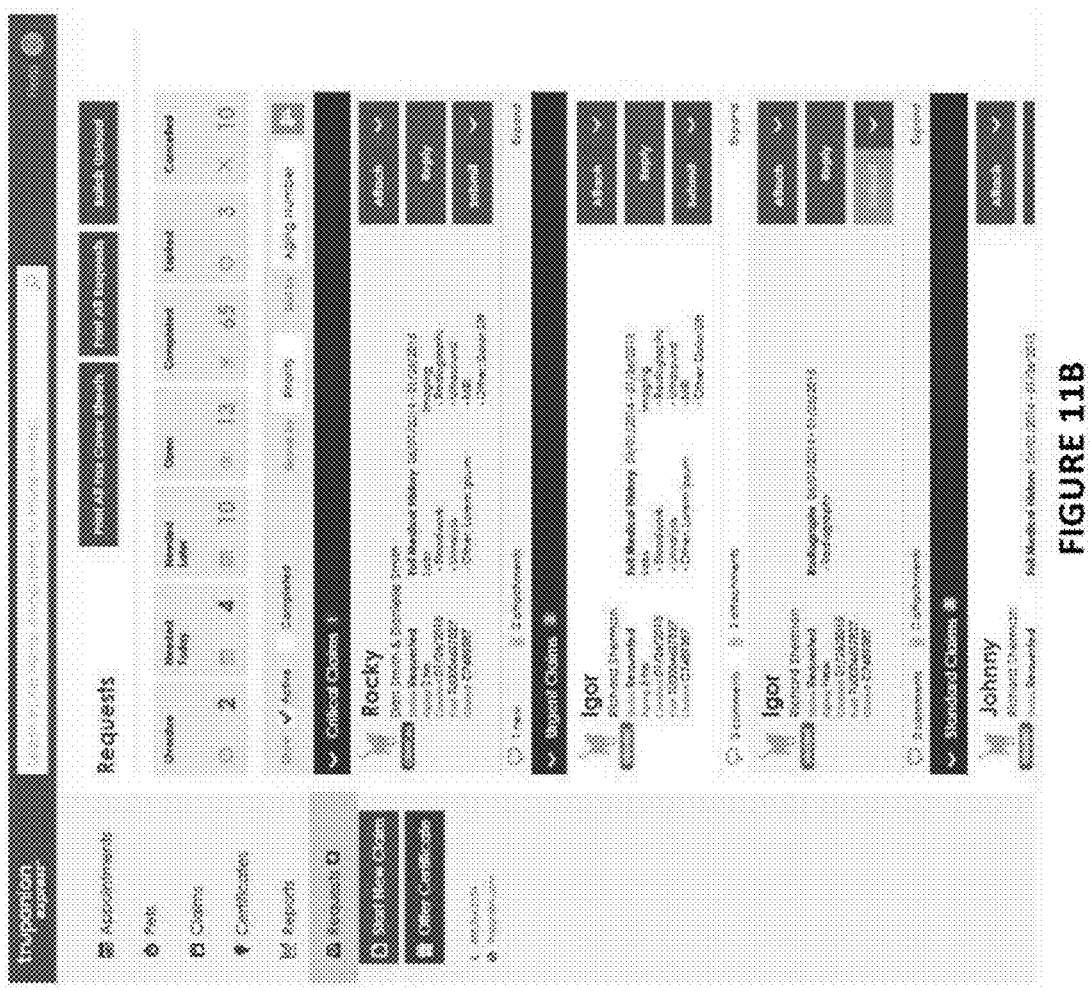
Figure 12A:
FIGS. 12A and 12B illustrates an example of a user interface for completing medical records requests.
Figure 12B:
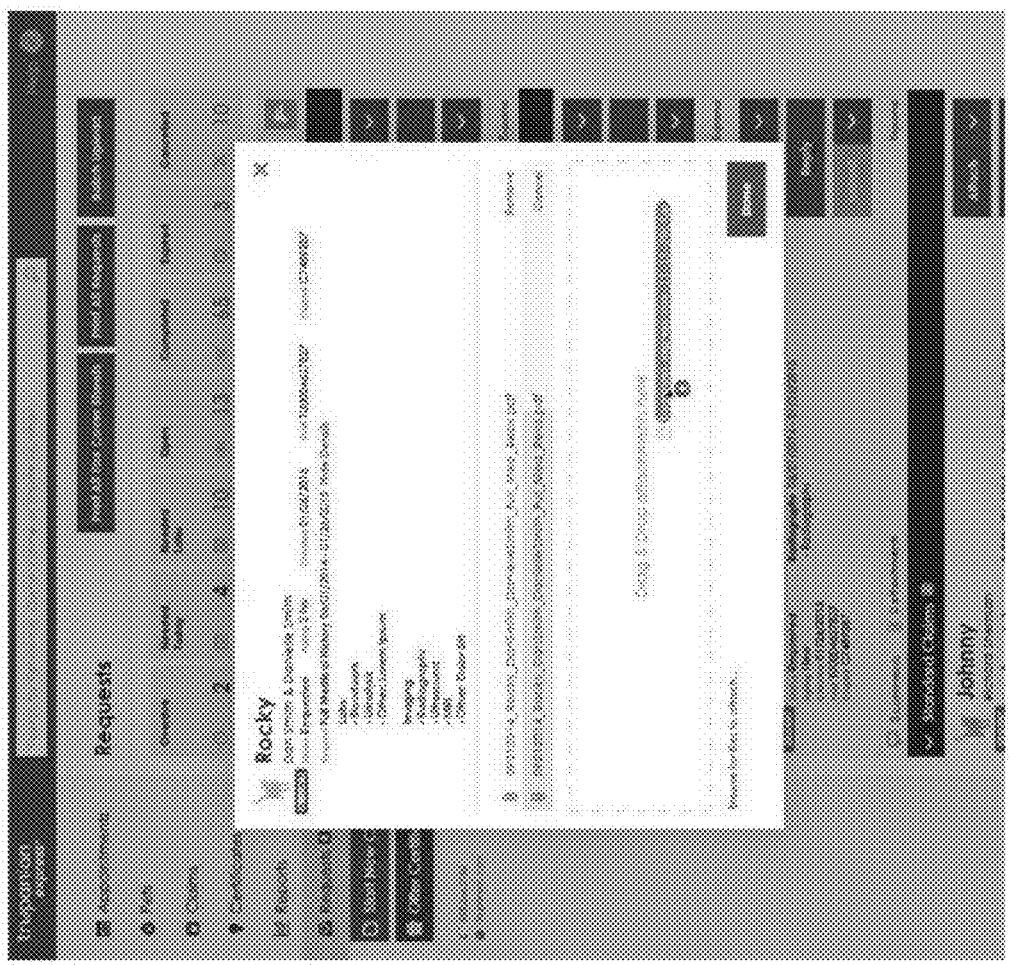

FIG. 10 illustrates a method (800) for requesting and receiving medical record information used to determine a pet's eligibility for insurance coverage. When the pet insurance system is generating the eligibility the computing device 200 and the pet insurance systems 106C may obtain a history of a pet from any veterinary practice that has seen the pet in the past through the data integration component 200. The pet insurance components (106C) may then structure that data and generate an eligibility of coverage. The system may then display that eligibility of coverage to the users of the system which allows all of the users to rapidly see the coverage status for a pet in a user interface (refer to FIG. 9). During the course of collecting medical record information for a pet, it may be required for a hospital to respond directly to requests for information utilizing the user interface of the pet insurance system. FIGS. 11A and 11B illustrate an example of a user interface for notification of a request for medical records and tracking of medical records requests. FIGS. 12A and 12B illustrate an example of a user interface for submitting requested records and completing medical records requests.

Figure 13:
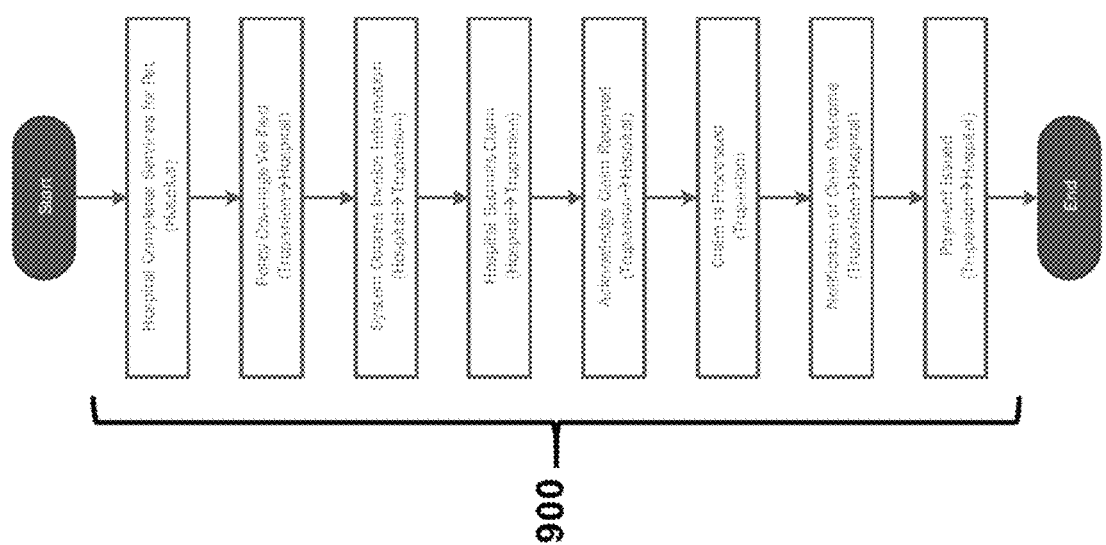
FIG. 13 illustrates a method for submitting and processing a claim in the pet insurance system.
Figure 14A:
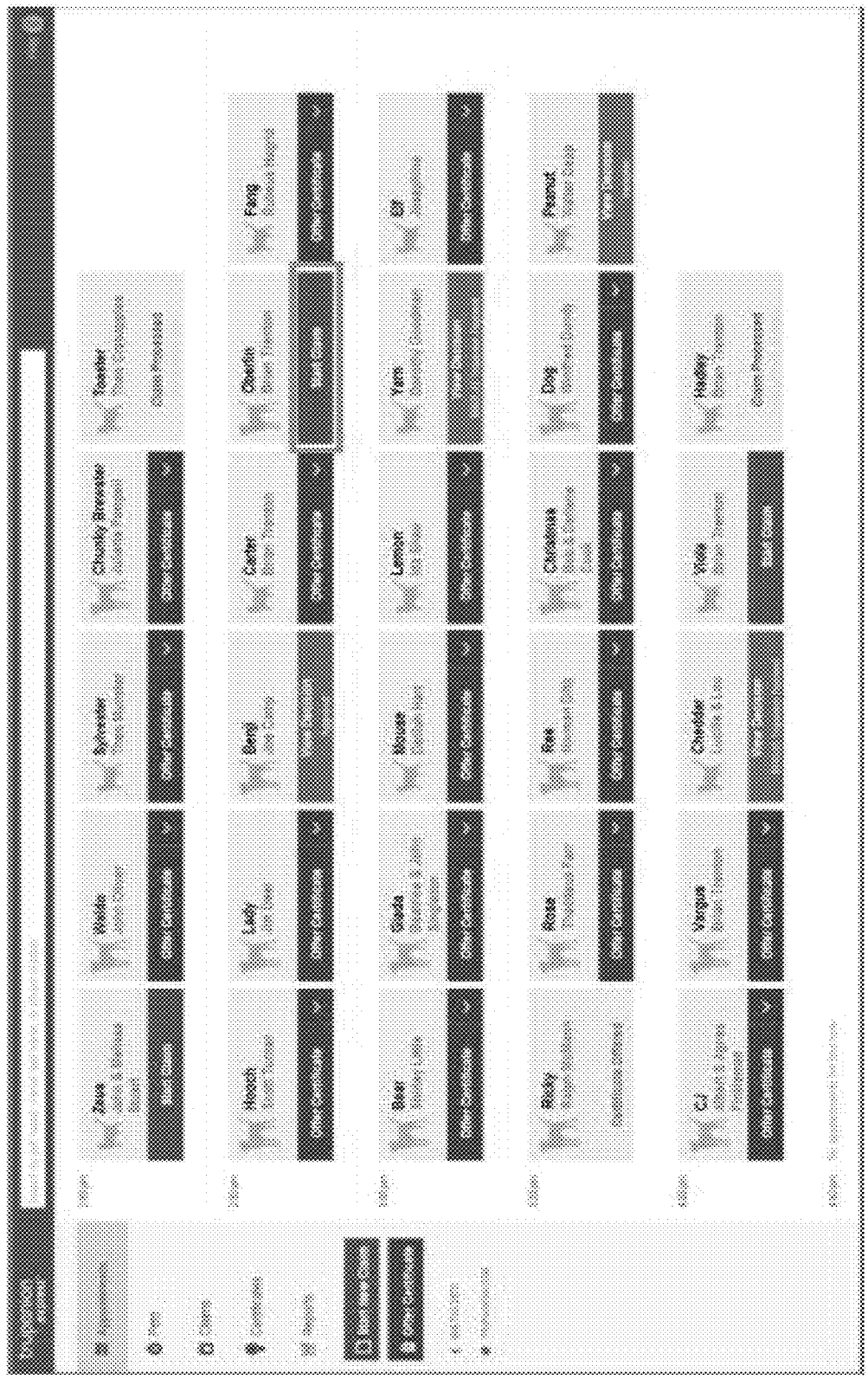
FIGS. 14A and 14B illustrate an example of a user interface for submitting claims in the pet insurance system.
Figure 14B:

FIG. 13 illustrates a method (900) for submitting and processing a claim in the pet insurance system. Since the backend component and each computing device in the veterinary practice are integrated, as seen in FIG. 2, and the system has determined a patient's eligible coverage, an insurance claim may be quickly processed by the claims processing component of the pet insurance component (106C). A claim starts when an employee or doctor of a veterinary hospital completes services for a pet and the veterinary practice submits a claim (see FIG. 14A for an example) for the treatment using a claim form (such as shown in FIG. 14B) that is generated by the client/browser (201) in combination with the data integration agent (200). The pet insurance company, through the pet insurance systems 106C, may then process the claim. The pet insurance company has the status of the pet's eligibility for coverage and this is able to quickly approve or deny the insurance claim for the pet. If the claim is approved, the claim may be paid directly to the veterinary practice (in one implementation, electronically via ACH) and then the pet owner pays their portion to the veterinary practice. In this manner the system allows a claim to be quickly processed and then paid if the insurance claim is approved.

Figure 15:
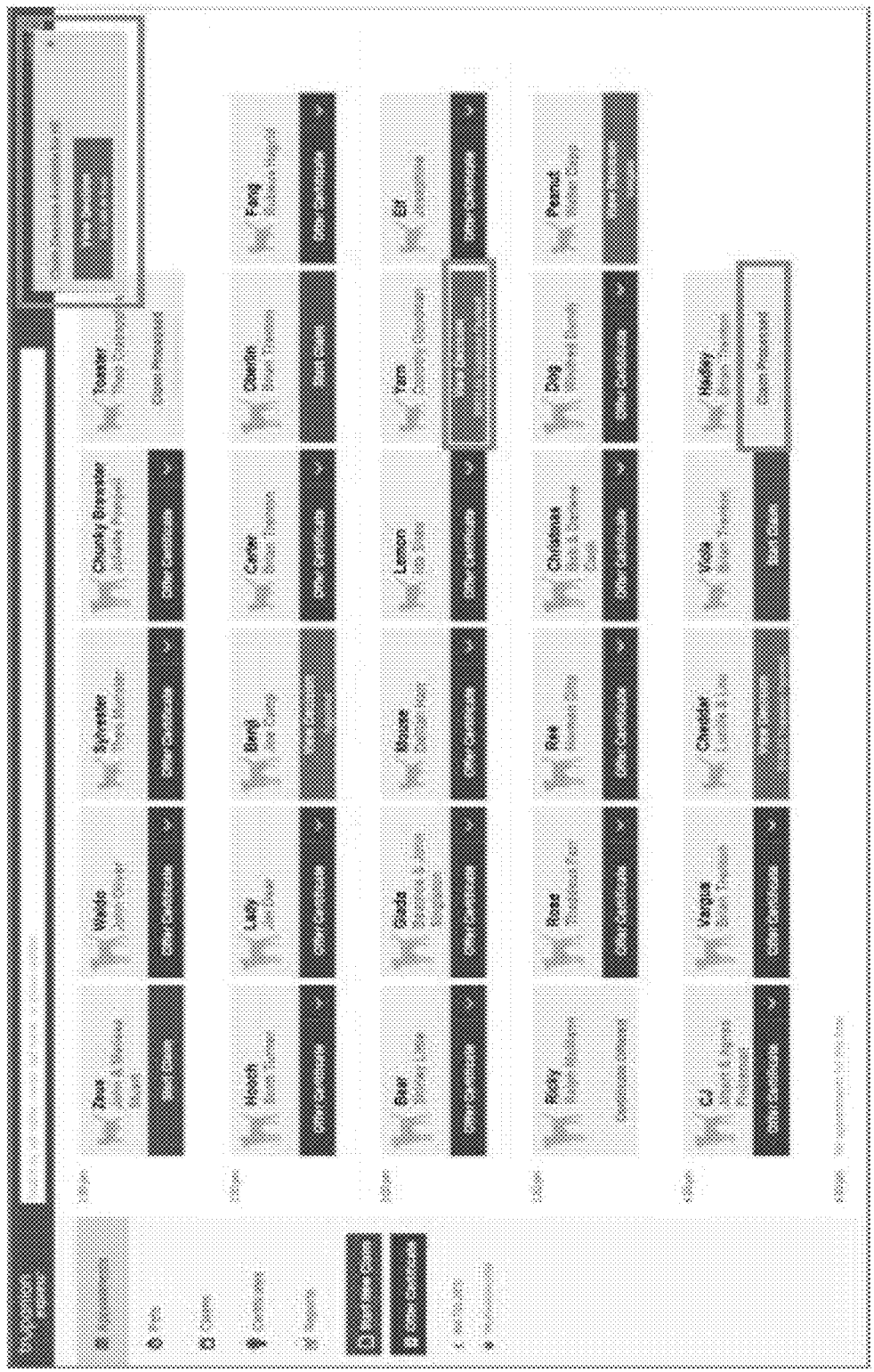
FIG. 15 illustrates an example of a user interface indicating claims outcomes.

FIG. 15 is an example of a user interface of pet insurance system 100 highlighting display of communication from Trupanion to the veterinary practice claim outcome information.

Figure 16:
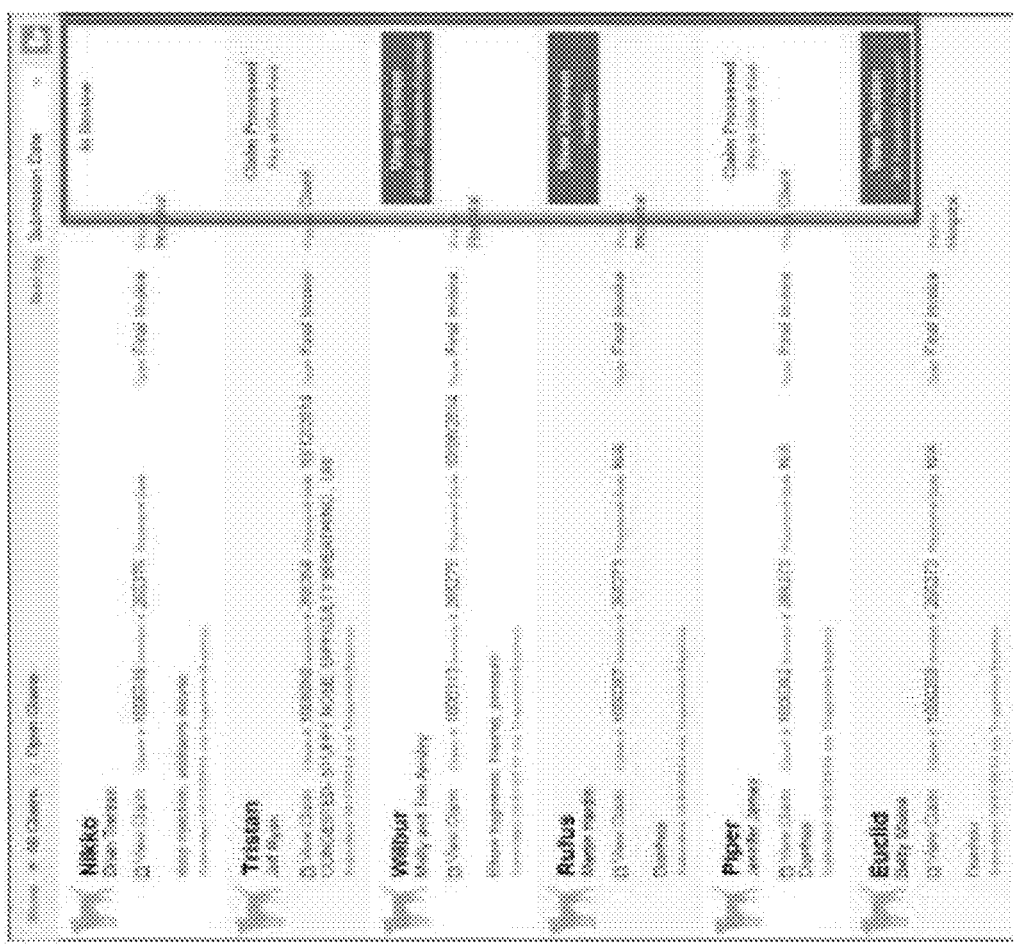
FIG. 16 illustrates an example of a user interface for claims submission and payment tracking.

FIG. 16 is an example of a user interface for pet insurance system 100 for tracking of the status of claims submitted and the outcomes and payments for those claims.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A pet medical insurance system, comprising:
a backend component;
one or more user computing devices coupled to the backend component over a communication path, each user computing device being configured for use by an owner of a patient and having a processor, memory and a plurality of lines of computer code;
a computer system at a veterinary practice connected to the backend component over the communication path, the computer system comprising:
a processor;
memory; and
a first practice information management system of the veterinary practice having one or more modules for managing the veterinary practice; and
a client having a user interface and being in communication with the practice information management system;
a plug-and-play data integration system connected to the first practice information management system of the computer system and in communication with the backend component, wherein the plug-and-play data integration system receives data from the practice management system, maps the data according to the backend system and sends the mapped data to the backed system, thereby limiting the data traffic between the backend component and the first practice information management system, the plug-and-play data integration system being plug-and-play integratable with a second or more different practice information management systems for connection thereto;
the backend component comprising:
a processor,
memory,
a database, and
a plurality of lines of computer code configured to:
communicate with the plug-and-play data integration system to request data from the secure practice management system, the plug-and-play data integration system accessing data from the secure practice management system of each veterinary practice,
receive from the plug-and-play data integration system one or more pieces of data about the one or more treatments and procedures for a particular patient by each veterinary practice from the secure practice management system, and
store the one or more pieces of data about the one or more treatments and procedures for a particular patient by the veterinary practice in the database;
each of the one or more user computing devices further configured to:
generate the user interface in the client,
communicate with the backend component to request insurance coverage for a particular patient, and
receive an electronic insurance offer from the backend component and allow activation of the insurance offer; and
the backend component further configured to:
receive the request for insurance coverage for the particular patient, generate an electronic eligibility of insurance coverage for the patient that is stored in the database when the insurance has been activated by the owner, and
communicate the electronic eligibility of insurance coverage for the patient to the veterinary practice computer system through the plug-and-play data integration system;
the veterinary practice computer system further configured to display the communicated electronic eligibility of insurance coverage as a patient insurance coverage status to the veterinary practice; and
the backend component further configured to:
programmatically process a claim for one or more treatments and procedures for the particular patient based on the insurance coverage status of the patient, and
electronically pay an amount to the veterinary practice for the one or more provided treatments and procedures at the time of completion of the one or more provided treatments and procedures.

2. The system of claim 1, wherein the backend component further comprises a user interface component that is configured to generate a user interface containing information about the particular animal for the veterinary practice.

3. The system of claim 1, wherein the backend component further comprises one or more databases that store one or more pieces of data about one or more of treatments and procedures for the particular animal by the veterinarian or an employee of the veterinary practice.

4. The system of claim 2, wherein the user interface component is configured to generate an insurance claim form.

5. The system of claim 1 wherein the backend component further comprises one or more computing resources that host the backend component.

6. The system of claim 5, wherein one or more computing resources further comprise a processor and wherein the backend component further comprises a plurality of lines of computer code that are executed by the processor.

7. The system of claim 5, wherein each of the one or more computing resources is one of a server computer and/or cloud computing resource(s).

8. A method of providing insurance for one of veterinary treatment and veterinary procedures using a backend component implemented on a computer, comprising:
receiving, by a services component of the backend component from an insurance component used by each veterinary practice that is remote from the backend component, one or more pieces of data about one of a treatment and a procedure for a particular animal;
storing the one or more pieces of data about the one or more treatments and procedures for a particular patient by the veterinary practice in a database of the backend component;
generating, on one or more computing devices capable of being coupled to the backend component, a user interface to communicate with the backend component to request insurance coverage for an animal and to receive an insurance offer from the backend component;

mapping data from a first practice system of the veterinary practice to the insurance component, by a plug-and-play data integration system connected to the first practice system and in communication with the backend component, the plug-and-play data integration system:
receiving data from the first practice system;
mapping the data according to the insurance component; and
sending the mapped data to the insurance component, thereby limiting the data traffic between the insurance component and the first practice system to create efficient correspondence between the insurance component and the practice system and improve the enrollment and claim processing of the animal, the plug-and-play data integration system being plug-and-play integratable with a second or more practice systems for connection thereto;
enrolling, by an enrollment processing component, the owner of the animal for insurance for the animal upon receipt of the request for the insurance of the animal and issuing the insurance offer for the animal;
programmatically generating, using a claims processing component of the backend component, an eligibility of insurance coverage for the animal when the insurance has been activated by the owner, the eligibility of insurance coverage being stored in the database displaying, at both the veterinary practice that provided one or more treatments and procedures for the animal and at the user computing device, a insurance coverage status; and
programmatically processing, using the a claims processing component of the backend component, a claim for one of the treatment(s) and the procedure(s) for the animal, wherein the claim based on the eligibility of insurance coverage status of the animal and paying an amount to the veterinary practice for the one or more provided treatments and procedures.

9. The method of claim 8 further comprising generating a user interface containing information about the animal.

10. The method of claim 8 further comprising storing the one or more pieces of data about the treatment and procedure for the animal.

11. The method of claim 9 further comprising generating an insurance claim form.

12. The method of claim 8, wherein enrolling the owner of the animal further comprises activating the offer for insurance coverage.

13. A pet insurance system, comprising:
a first veterinary practice system of a veterinary practice having a pet insurance component;
a backend component remote from the veterinary practice comprising a processor, memory, a database and a plurality of lines of computer code configured to:
communicate with the insurance component used by the first veterinary practice system over a communications path, receive from the insurance component over the communications path, one or more pieces of data about one of a treatment and a procedure for an animal by the veterinary practice and store the
one or more pieces of data about the one or more treatments and procedures for the animal by the veterinary practice in the database;
one or more user computing devices capable of being coupled to the backend component, each computing device comprising a processor, memory and a plurality of lines of computer code configured to:
generate user interface, communicate with the backend component to request insurance coverage for the animal and receive an insurance offer from the backend component;
a computing device at each veterinary practice having a processor, memory and a plurality of lines of computer code in a data integration component configured to:
connect to the first veterinary practice system of the veterinary practice and communicate between the practice system and the backend component;
the backend component further configured to receive the insurance coverage request for the animal, programmatically issue the insurance offer to the owner of the animal for insurance for the animal, generate an eligibility of insurance coverage for the animal when the insurance has been activated by the owner that is stored in the database and displayed at the veterinary practice that provided one or more treatments and procedures for the animal as patient insurance coverage status and displayed at the user computing device as patient insurance coverage status, programmatically process a claim for the treatment(s) and procedure(s) for the animal based on the eligibility of insurance coverage status of the animal and pay an approved claim amount to the veterinary practice for the one or more provided treatments and procedures; and
a plug-and-play data integration system connected to the first veterinary practice system of the veterinary practice and in communication with the backend component, the plug-and-play data integration system receives data from the veterinary practice system, maps the data according to the backend system and sends the mapped data to the backed system, thereby limiting the data traffic between the backend component and the first veterinary practice system, the plug-and-play data integration system being plug-and-play integratable with a second or more different practice systems of the veterinary practice for connection thereto.

14. The system of claim 13, wherein the backend component further comprises a user interface component that is configured to generate a user interface containing information about the particular animal for the veterinary practice.

15. The system of claim 13, wherein the backend component is configured to generate an insurance claim.

16. The system of claim 14, wherein the user interface component is configured to generate an insurance claim.

17. The system of claim 13, wherein the backend component further comprises a processor and wherein the backend component further comprises a plurality of lines of code that are executed by the processor.

18. The system of claim 17, wherein each of the one or more computing resources is one of a server computer and/or cloud computing resource(s).

19. The system of claim 17, wherein each of the one or more computing resources is one of a server and/or cloud computing resource(s).

20. The system of claim 13 further comprising one or more computing devices wherein each computing device is configured to allow the owner of the particular animal to activate insurance coverage.

21. The system of claim 20, wherein each computing device further comprises a processor and a browser application executed by the processor to interact with the backend component.

22. The system of claim 13 wherein the pet insurance component further comprises a plurality of lines of computer code.

* * * * *